(12) United States Patent
Connell, II

(10) Patent No.: US 7,819,525 B2
(45) Date of Patent: Oct. 26, 2010

(54) AUTOMATIC DIRECT GAZE DETECTION BASED ON PUPIL SYMMETRY

(75) Inventor: Jonathan H. Connell, II, Cortlandt-Manor, NY (US)

(73) Assignee: International Business Machines Corporation, Armonk, NY (US)

( * ) Notice: Subject to any disclaimer, the term of this patent is extended or adjusted under 35 U.S.C. 154(b) by 62 days.

(21) Appl. No.: 12/371,607

(22) Filed: Feb. 15, 2009

(65) Prior Publication Data

US 2010/0208207 A1    Aug. 19, 2010

(51) Int. Cl.
*A61B 3/10* (2006.01)
(52) U.S. Cl. .................. 351/204; 351/209; 351/210; 351/246; 382/103
(58) Field of Classification Search .......... 351/204, 351/205, 209, 210, 246; 382/103, 117
See application file for complete search history.

(56) References Cited

U.S. PATENT DOCUMENTS

| | | | |
|---|---|---|---|
| 5,155,516 A | 10/1992 | Shindo | |
| 5,293,535 A | 3/1994 | Sensui | |
| 5,428,413 A | 6/1995 | Shindo | |
| 5,557,364 A | 9/1996 | Shindo et al. | |
| 5,561,973 A | 10/1996 | St. Germain | |
| 5,608,489 A | 3/1997 | Ozakl | |
| 5,818,954 A * | 10/1998 | Tomono et al. | 382/115 |
| 6,152,563 A | 11/2000 | Hutchinson et al. | |
| 6,246,779 B1 * | 6/2001 | Fukui et al. | 382/103 |
| 6,331,168 B1 | 12/2001 | Socci et al. | |
| 7,068,813 B2 * | 6/2006 | Lin | 382/103 |
| 7,458,901 B2 | 12/2008 | Hoganson | |
| 7,460,940 B2 | 12/2008 | Larsson et al. | |
| 7,717,561 B2 * | 5/2010 | Knaan et al. | 351/210 |
| 2006/0189405 A1 | 8/2006 | Hoganson | |

* cited by examiner

*Primary Examiner*—Huy K Mai
(74) *Attorney, Agent, or Firm*—Anna L. Linne; Ronald A. D'Alessandro; Keohane & D'Alessandro PLLC

(57) ABSTRACT

The present invention provides a system and methods for direct gaze detection based on pupil symmetry. The system and methods work by first finding the user's eyes in a video camera image and measuring the symmetry of the pupil region. If this pupil region is close to round, the invention determines that the user is looking nearly directly or close to directly at the camera, or has direct gaze at the camera. This technique handles both eye motions and head motions (e.g., the gaze may shift with or without the head being turned).

20 Claims, 5 Drawing Sheets

AUTOMATIC DIRECT GAZE DETECTION BASED ON PUPIL SYMMETRY

FIELD OF THE INVENTION

The present invention provides for direct gaze detection based on pupil symmetry.

BACKGROUND OF THE INVENTION

There are many applications for detecting when a human user is looking directly at a device. One such application is self-service kiosks. The kiosk may be in a general attention attracting mode with flashy graphics until someone actually looks at the device. At this point, it may launch a targeted promotion because it has the user's attention.

Kiosks can also be activated by simple proximity sensors or by machine vision systems employing techniques such as background subtraction. However, these solutions only assure that a person is nearby, not that he is looking at the device.

Another application is operator alertness monitoring. At regular intervals the operator of a machine may be required to look at various task-relevant areas or directions. For instance, an alert driver of a car needs to look forward through the windshield and occasionally at the rearview mirror. If this does not occur, or only one point is looked at, the driver may have become drowsy. The proper alternation of gaze can be determined by placing a gaze detector at each special point, i.e., the base of the windshield and in the rearview mirror.

There are also a number of driver alertness systems. Many of these are based on blink frequency or eyelid closing rate. As such, they do not ensure that a driver is paying attention to the important aspects of his environment (e.g., he may be facing the passenger).

There are many eye-tracking devices on the market. However, many of them must be worn by the user. Others are bulky or have a limited range of acceptable positions for the user's head.

SUMMARY OF THE INVENTION

The present invention provides for direct gaze detection based on pupil symmetry. The system works by first finding the user's eyes in a video camera image and measuring the symmetry of the pupil region. Pupil and pupil region may be used interchangeably. If this pupil region is close to round, the system determines that the user is looking nearly directly or close to directly at the camera, or has direct gaze at the camera. This technique handles both eye motions and head motions (e.g., the gaze may shift with or without the head being turned).

One embodiment of the present invention discloses a method for direct gaze detection based on pupil symmetry comprising finding one or both of a user's pupil regions of eyes of the user in a video camera image from a video camera, measuring a symmetry of a pupil region, determining if the pupil region is close to round and if the pupil region is close to round, determining that the user is looking at the video camera.

Another embodiment of the present invention is a system for direct gaze detection based upon pupil symmetry, the system comprising a video camera for finding eyes and pupil regions of a user, the video camera having an optical axis, a first set of infrared light-emitting diodes (LEDs) for shining infrared light into the user's eyes so that the video camera may acquire a first image of the user's pupil regions, a second set of infrared LEDs for shining infrared light into the user's eyes so that the video camera may acquire a second image of the user's pupil regions and a processing unit for computing a pixel-by-pixel difference of the first acquired image and the second acquired image for identifying possible retroreflectors.

In yet another embodiment, a computer program product is embodied in a computer readable medium for operating in a system comprising a processing unit, a memory, a bus, and input/output (I/O) interfaces, for implementing a method for direct gaze detection of a user into a video camera, the method comprising finding one or both of a user's pupil regions of eyes of the user in a video camera image from a video camera, measuring a symmetry of at least pupil region, determining if the at least one pupil region is close to round and if the at least one pupil region is close to round, determining that the user is looking at the video camera.

Another embodiment describes a method for deploying computing infrastructure comprising integrating computer-readable code into a computing system, wherein the code in combination with the computing system is capable of performing a process for detecting a direct gaze of a user into a video camera, the process comprising finding one or both of a user's pupil regions of eyes of the user in a video camera image from a video camera, measuring a symmetry of at least pupil region, determining if the at least one pupil region is close to round and if the at least one pupil region is close to round, determining that the user is looking at the video camera.

BRIEF DESCRIPTION OF THE DRAWINGS

These and other features of this invention will be more readily understood from the following detailed description of the various aspects of the invention taken in conjunction with the accompanying drawings in which.

The drawings are not necessarily to scale. The drawings are merely schematic representations, not intended to portray specific parameters of the invention. The drawings are intended to depict only typical embodiments of the invention, and therefore should not be considered as limiting the scope of the invention.

DETAILED DESCRIPTION OF THE INVENTION

The present invention comprises a system and methods for direct gaze detection based on pupil symmetry. The pupil is a central transparent area0020 (which typically shows as black and is round in shape). The area surrounding the pupil is the iris. A white outer area is the sclera, the central transparent part of which is the cornea. The system first finds the user's eyes in a video camera image and then measures the symmetry, or shape, of the pupil region. If this region is round or close to round, the user has direct gaze at the camera or is looking nearly directly at the camera. If this region is not close to round or more elliptical, the user has direct gaze at the camera or is looking nearly directly at the camera. This technique handles both eye motions and head motions (e.g., the gaze may shift with or without the head being turned).

While the actual gaze direction (angle in degrees) might be estimated given enough resolution on the eye region, typically this is not available. With low resolution imagery (e.g., the user is far from the camera), the detection of symmetry is much easier to achieve than the inference of a reliable gaze angle. Mere symmetry detection is also more robust to phenomena such as the closing down of the iris in high light conditions (which makes the pupil smaller).

Such a system has a number of advantages. First it can employ a normal video camera to give an adequate resolution (e.g., 10 pixel pupils) at reasonable range (several feet) and still allow some motion by the user. (In digital imaging, a pixel (picture element) is the smallest piece of information in an image.) It is also an unobtrusive, non-contact sensor that can be used with non-cooperative users (e.g., simple passersby of a kiosk). Finally, the computer processing of images that is required is fairly simple and can be implemented with a low cost processor. This is in contrast to a technique such as finding head angle by measuring nose position using stereo depth vision, which requires a second camera and much more computation.

Figure 1:
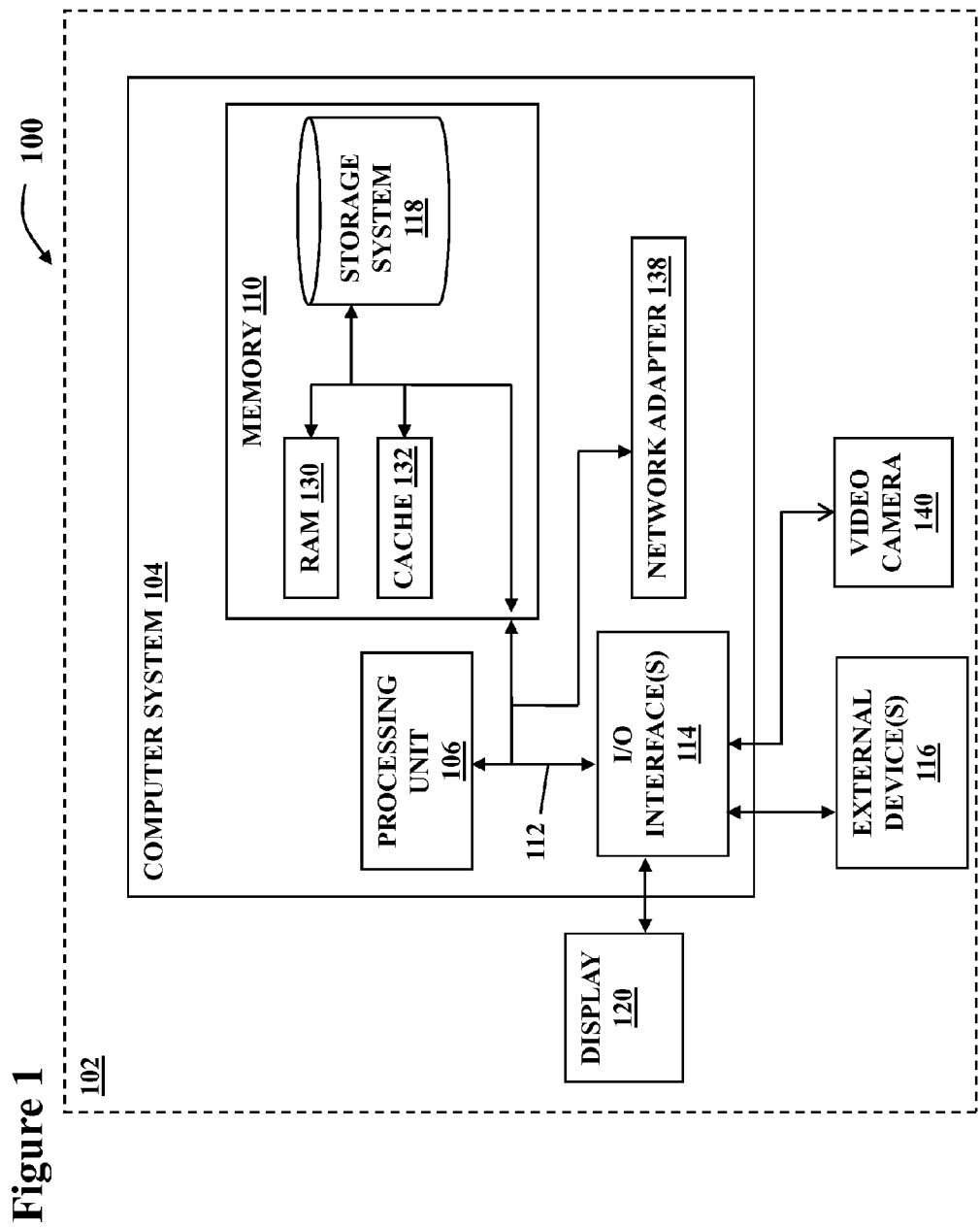
FIG. 1 shows a data processing system suitable for implementing an embodiment of the present invention.

A system, such as system 100, may have a data processing system, such as data processing system 102 shown in FIG. 1, suitable for storing and/or executing program code of the present invention, and may include a computer system, such as computer system 104, having at least one processing unit (processing unit 106) coupled directly or indirectly to memory elements (memory 110) through a system bus, such as system bus 112. Memory 110 may include local memory (RAM 130) employed during actual execution of the program code, bulk storage (storage 118), and cache memories (cache 132) that provide temporary storage of at least some program code in order to reduce the number of times code must be retrieved from storage 118 during execution. Input/output or I/O devices (such as display 120, and other external devices (external devices 116)), including but not limited to keyboards, pointing devices, etc., may be coupled to computer system 104 either directly or through intervening I/O controllers (I/O interface(s) 114). I/O interface(s) 114 may further couple video camera 140 for finding a user's eyes. Network adapter(s) (network adapter 138) may provide access to external networks.

Figure 2:
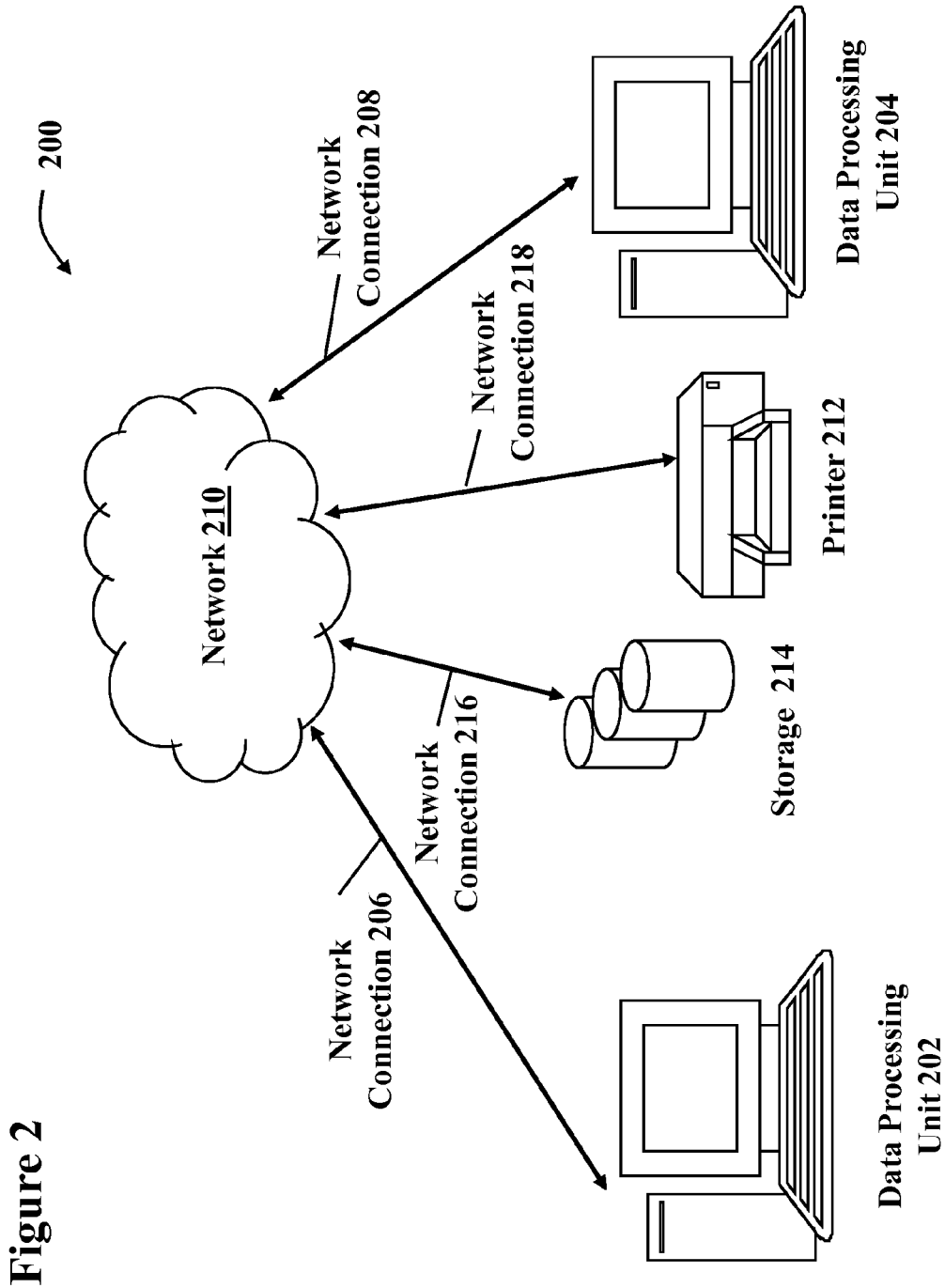
FIG. 2 shows a network for implementing an embodiment of the present invention.

FIG. 2 illustrates a networked system, such as system 200, to enable a data processing system (data processing unit 202) to be coupled through network connection(s) (network connection 206, 208, 216, 218) to other data processing systems (data processing unit 204), remote printers (printer 212) and/or storage devices (storage 214) through intervening private and/or public network(s) (network 210).

Figure 4:
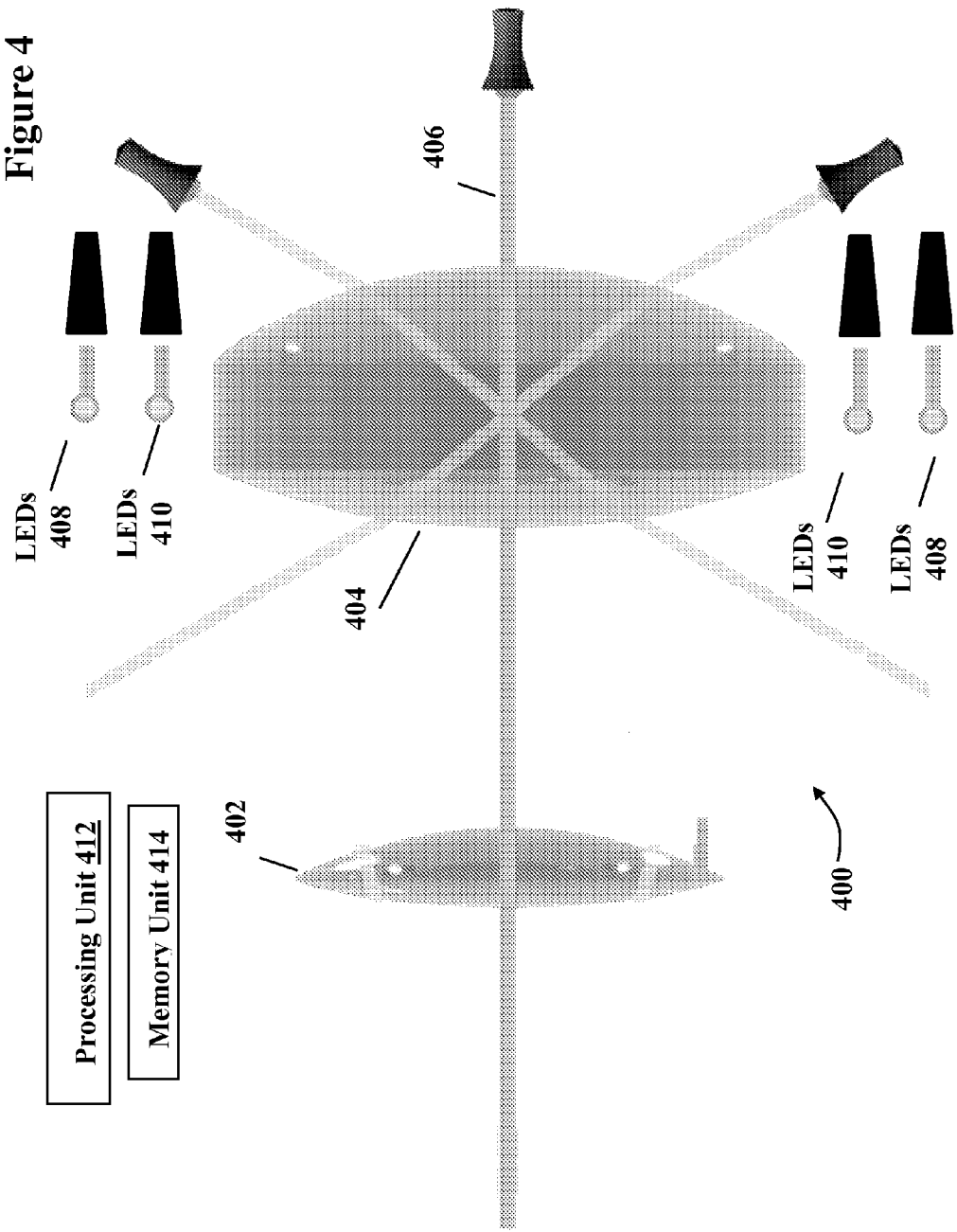
FIG. 4 illustrates an embodiment of the present invention having lenses, two sets of LEDs, and an optical axis.

Typically, the system first needs to find the pupils in the video image captured by video camera 140. A quick, simple, and reliable way to do this is to utilize the "red eye" effect. As shown in FIG. 4, a set of near-infrared light-emitting diodes (inner ring LEDs 408) positioned near optical axis 406 of camera 140 are turned on and an image of the environment is acquired. This is shown in method 500 in FIG. 5 which begins at 502 and continues to 504 where the digital image of the pupils is received, stored in memory unit 414 and processed by processing unit 412. This is accomplished by shining the inner ring LEDs 408 at the pupils. The near-infrared light is reflected off the back of the eye through the pupil and acquired by video camera 140. At 506, another image is then acquired by shining a similar set of LEDs (Outer Ring LEDs 410) further displaced from optical axis 406 of camera system 140 at the pupils. (In optics, the term optical axis is used to define a direction along which there is some degree of rotational symmetry. In an optical system, the optical axis is an imaginary line that defines the path along which light propagates through the system.) This is shown as 406 in FIG. 4 in system 400. For a system composed of simple lenses (Lens 402, Lens 404) and mirrors, optical axis 406 passes through the center of curvature of each surface, and coincides with the axis of rotational symmetry. The optical axis is often coincident with the system's mechanical axis, but not always, as in the case of off-axis optical systems.

Figure 3:
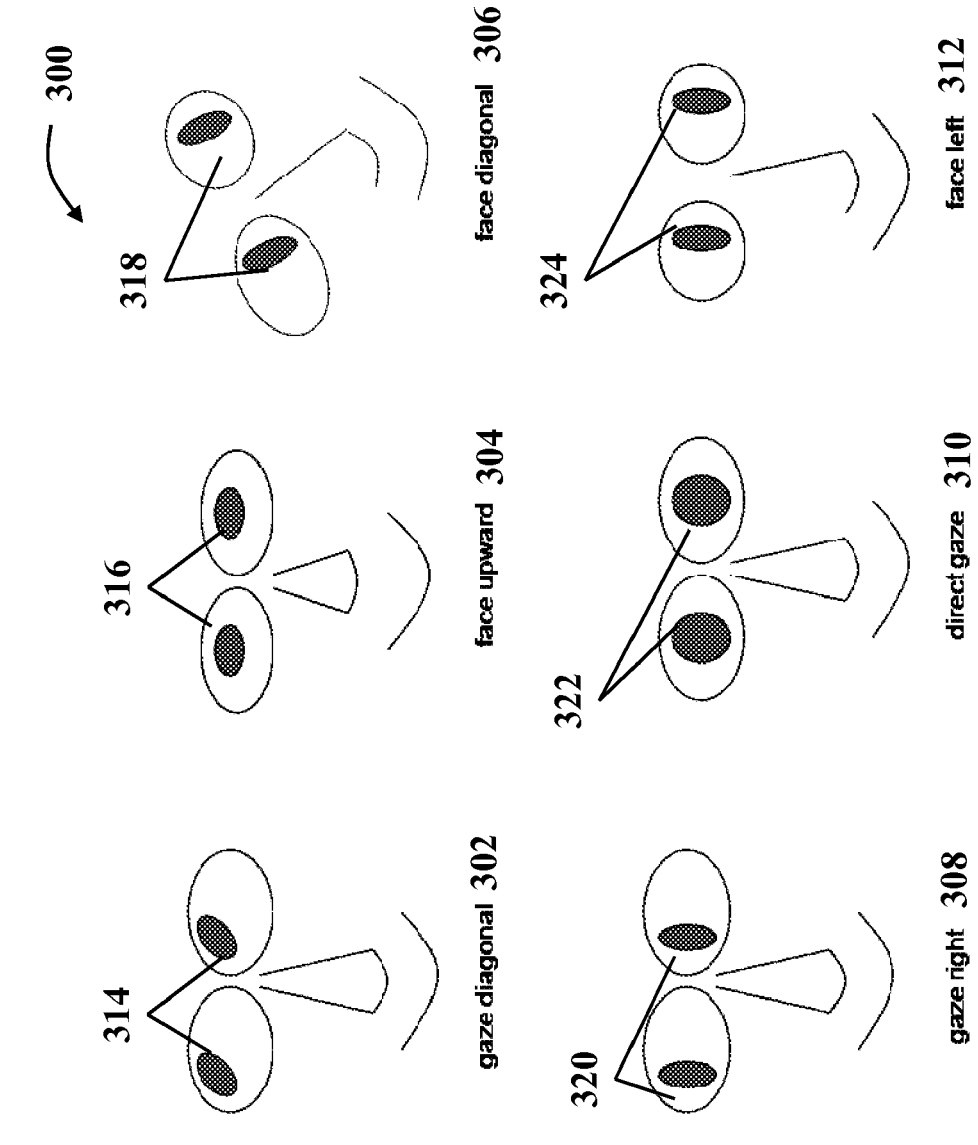
FIG. 3 illustrates various depictions of facial expressions that can be detected by the present invention.
Figure 5:
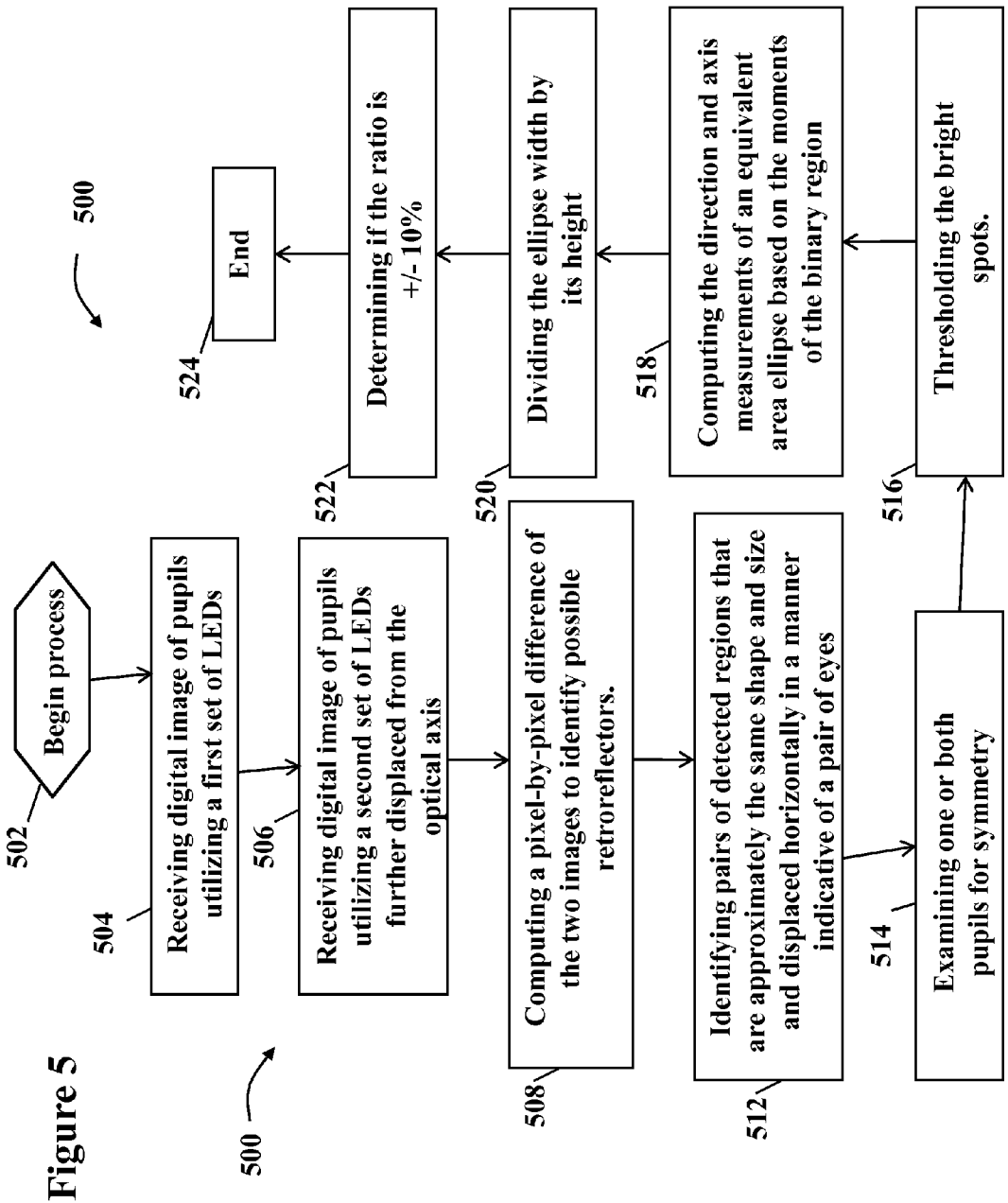
FIG. 5 illustrates one embodiment of the method for scanning a user's eyes and pupil regions and for determining whether the user is looking at the video camera.

A pixel-by-pixel difference of the two images is then computed to identify possible retroreflectors at 508 of FIG. 5. (A retroreflector (sometimes called a retroflector) is a device or surface that reflects light back to its source with a minimum scattering of light.) Next, at 512, the system identifies pairs of detected regions that are approximately the same shape and size and displaced side-by-side, typically horizontally, in a manner indicative of a pair of eyes. This is shown in FIG. 3 showing multiple facial expressions and face directions 300. For instance, gaze diagonal 302 has a pair of detected regions that are approximately the same shape and size and displaced horizontally in a manner indicative of a pair of eyes 314 gazing upwardly and to the left. Similarly, face upward 304 has a pair of eyes 316 pointing upwardly due to the face being directed in an upward direction. Face diagonal 306 has a pair of eyes 318 illustrates the face tilted at an angle. Gaze right face 308 has a pair of eyes 320 pointing toward the left. Direct gaze face 310 has eyes 322 pointing directly at the video camera. Face left 312 has eyes 324 pointed toward the left due the face pointed to the left.

One or both of the pupil regions is examined for symmetry at 514 in FIG. 5. This can be done by thresholding bright spots at 516, and computing the direction and axis measurements of an equivalent area ellipse based on the moments of the binary region at 518. The aspect ratio of the region is then defined as the ellipse width divided by its height. At 520, the ellipse width divided by its height. A ratio near one (e.g., +/−10%) is suggestive of a circle and hence is used to signal a direct gaze by a particular individual in the environment and, at 522, the aspect ratio is computed. For instance, if direct gaze face 310 has near or close to round pupil regions 322, the system determines that the user is directly gazing at the video camera. By contrast, the other faces have more elliptical pupil regions indicating that the user is not looking at the camera.

Many of these steps could be achieved by alternative means. Eyes can be found by template matching to a model eye(s) or by looking for time differences in a video stream that are induced by eye blink motions. Once an eye region is located, the pupil could be found by suitably thresholding to find the darkest spot in the region. Symmetry could then measured as above with the ellipse method or by other means. An alternative would be to convolve the central portion of the eye regions with matched filters tuned for different eye gaze angles (e.g. [−1 1 1] for left, [1 1 −1] for right, and [1 −1 1] for centered) and comparing their responses. Still another method would be to process a small patch of pixel intensities near the eye center using a neural network that has been trained with direct gaze examples and non-direct examples. This might be particularly useful for extremely low-resolution imagery where the size of the user's pupil is comparable to a pixel. Finally, the signaling of a direct gaze does not have to be done on a frame-by-frame basis but could instead involve integration over time. A direct gaze may be signaled when the last 20 images all had symmetric pupils, or when 80% of the video frames for the last second had symmetric pupils.

It should be understood that the present invention is typically computer-implemented via hardware and/or software. As such, client systems and/or servers will include computerized components as known in the art. Such components typically include (among others), a processing unit, a memory, a bus, input/output (I/O) interfaces, external devices, etc.

While shown and described herein as a system and method for direct gaze detection based on pupil symmetry, it is understood that the invention further provides various alternative embodiments. For example, in one embodiment, the invention provides a computer-readable/useable medium that includes computer program code to enable a computer infrastructure for direct daze detection based on pupil symmetry. To this extent, the computer-readable/useable medium includes program code that implements each of the various process steps of the invention. It is understood that the terms computer-readable medium or computer useable medium comprises one or more of any type of physical embodiment of the program code. In particular, the computer-readable/useable medium can comprise program code embodied on one or more portable storage articles of manufacture (e.g., a compact disc, a magnetic disk, a tape, etc.), on one or more data storage portions of a computing device, such as memory and/or storage system (e.g., a fixed disk, a read-only memory, a random access memory, a cache memory, etc.), and/or as a data signal (e.g., a propagated signal) traveling over a network (e.g., during a wired/wireless electronic distribution of the program code).

In another embodiment, the invention provides a computer-implemented method for direct daze detection based on pupil symmetry. In this case, a computerized infrastructure can be provided and one or more systems for performing the process steps of the invention can be obtained (e.g., created, purchased, used, modified, etc.) and deployed to the computerized infrastructure. To this extent, the deployment of a system can comprise one or more of (1) installing program code on a computing device, such as computer system from a computer-readable medium; (2) adding one or more computing devices to the computer infrastructure; and (3) incorporating and/or modifying one or more existing systems of the computer infrastructure to enable the computerized infrastructure to perform the process steps of the invention.

As used herein, it is understood that the terms "program code" and "computer program code" are synonymous and mean any expression, in any language, code or notation, of a set of instructions intended to cause a computing device having an information processing capability to perform a particular function either directly or after either or both of the following: (a) conversion to another language, code or notation; and/or (b) reproduction in a different material form. To this extent, program code can be embodied as one or more of: an application/software program, component software/a library of functions, an operating system, a basic I/O system/driver for a particular computing and/or I/O device, and the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method for direct gaze detection based on pupil symmetry comprising:

finding one or both of a user's pupil regions of eyes of the user in a video camera image from a video camera;
measuring a symmetry of a pupil region;
determining if the pupil region is close to round; and
if the pupil region is close to round, determining that the user is looking at the video camera.

2. The method as defined in claim 1 further comprising utilizing the video camera to find the user's pupil regions in the video camera image positioned away from the user's eyes.

3. The method as defined in claim 2 further comprising positioning the video camera several feet from the user's eyes.

4. The method as defined in claim 3 further comprising capturing video camera images of the user's pupil regions and processing the images.

5. The method as defined in claim 1 further comprising finding the user's pupil regions in the image using a red eye effect.

6. The method as defined in claim 5 wherein the camera has an optical axis, the method further comprising shining infrared light from a first set of infrared light-emitting diodes (LEDs) near the optical axis of the camera and acquiring a first image of the user's pupil regions.

7. The method as defined in claim 6 further comprising acquiring a second image by shining a second infrared light from a second set of LEDs, the second set of LEDs being further displaced from the optical axis of the camera than the first set of infrared LEDs.

8. The method as defined in claim 7 further comprising computing a pixel-by-pixel difference of the first acquired image and the second acquired image for identifying possible retroreflectors.

9. The method as defined in claim 8 further comprising identifying a pair of detected pupil regions that are approximately the same shape and size and displaced horizontally in a manner indicative of a pair of eyes.

10. The method as defined in claim 9 further comprising examining at least one pupil region for symmetry by thresholding bright spots and computing direction and axis measurements of an equivalent area ellipse based on moments of a binary region.

11. The method as defined in claim 1 further comprising finding the pupil regions by template matching to a model eye.

12. The method as defined in claim 1 further comprising finding the pupil regions by looking for time differences in a video stream that are induced by eye blink motions.

13. A system for direct gaze detection based upon pupil symmetry, the system comprising:
a video camera for finding eyes and pupil regions of a user, the video camera having an optical axis;
a first set of infrared light-emitting diodes (LEDs) for shining infrared light into the user's eyes so that the video camera may acquire a first image of the user's pupil regions;
a second set of infrared LEDs for shining infrared light into the user's eyes so that the video camera may acquire a second image of the user's pupil regions; and
a processing unit for computing a pixel-by-pixel difference of the first acquired image and the second acquired image for identifying possible retroreflectors.

14. The system as defined in claim 13 further comprising a memory unit for storing a model eye template wherein the processing unit further finds pupil regions by comparing the acquired images with the model eye template.

15. A computer program product embodied in a computer readable medium for operating in a system comprising a processing unit, a memory, a bus, and input/output (I/O) interfaces, for implementing a method for direct gaze detection of a user into a video camera, the method comprising:

finding one or both of a user's pupil regions of eyes of the user in a video camera image from a video camera;

measuring a symmetry of at least pupil region;

determining if the at least one pupil region is close to round; and if the at least one pupil region is close to round, determining that the user is looking at the video camera.

16. The computer program product as defined in claim 15 wherein the camera has an optical axis and further wherein the method further comprises shining infrared light from a first set of infrared light-emitting diodes (LEDs) near the optical axis of the camera and acquiring a first image of the user's pupil regions, acquiring a second image by shining a second infrared light from a second set of LEDs, the second set of LEDs being further displaced from the optical axis of the camera than the first set of infrared LEDs and computing a pixel-by-pixel difference of the first acquired image and the second acquired image for identifying possible retroreflectors.

17. The computer program product as defined in claim 16 wherein the method further comprises identifying a pair of detected pupil regions that are approximately the same shape and size and displaced horizontally in a manner indicative of a pair of eyes.

18. The computer program product as defined in claim 17 wherein the method further comprises examining at least one pupil region for symmetry by thresholding bright spots and computing direction and axis measurements of an equivalent area ellipse based on moments of a binary region.

19. A method for deploying computing infrastructure comprising integrating computer-readable code into a computing system, wherein the code in combination with the computing system is capable of performing a process for detecting a direct gaze of a user into a video camera, the process comprising:

finding one or both of a user's pupil regions of eyes of the user in a video camera image from a video camera;

measuring a symmetry of at least pupil region;

determining if the at least one pupil region is close to round; and if the at least one pupil region is close to round, determining that the user is looking at the video camera.

20. The method for deploying computing infrastructure as defined in claim 19 wherein the camera has an optical axis and further wherein the process further comprises shining infrared light from a first set of infrared light-emitting diodes (LEDs) near the optical axis of the camera and acquiring a first image of the user's pupil regions, acquiring a second image by shining a second infrared light from a second set of LEDs, the second set of LEDs being further displaced from the optical axis of the camera than the first set of infrared LEDs and computing a pixel-by-pixel difference of the first acquired image and the second acquired image for identifying possible retroreflectors.

\* \* \* \* \*